(12) United States Patent
Yanev et al.

(10) Patent No.: US 10,133,849 B2
(45) Date of Patent: Nov. 20, 2018

(54) MERCHANDIZING, SOCIALIZING, AND/OR GAMING VIA A PERSONAL WELLNESS DEVICE AND/OR A PERSONAL WELLNESS PLATFORM

(75) Inventors: Kostadin Dimitrov Yanev, Alamo, CA (US); Angel Georgiev Vassilev, Sofia (BG); Ivo Kostadinov Yanev, Sofia (BG)

(73) Assignee: ACTIVBODY, INC., La Jolla, CA (US)

( * ) Notice: Subject to any disclaimer, the term of this patent is extended or adjusted under 35 U.S.C. 154(b) by 0 days.

(21) Appl. No.: 13/527,437

(22) Filed: Jun. 19, 2012

(65) Prior Publication Data

US 2013/0337975 A1 Dec. 19, 2013

(51) Int. Cl.
*A61N 1/36* (2006.01)
*G06F 19/00* (2018.01)
(Continued)

(52) U.S. Cl.
CPC ....... *G06F 19/3481* (2013.01); *A61N 1/0452* (2013.01); *A61N 1/36003* (2013.01);
(Continued)

(58) Field of Classification Search
CPC ....... A63B 24/00; A63B 5/22; A63B 2220/00; A63B 21/1492; A63B 21/1496; A63B 23/16
(Continued)

(56) References Cited

U.S. PATENT DOCUMENTS 4,577,625 A  3/1986 Lohati et al. ............. 128/57
4,702,108 A 10/1987 Amundsen
(Continued)

FOREIGN PATENT DOCUMENTS

CN  201270095  8/2009
EP  2 284 646   2/2011
(Continued)

OTHER PUBLICATIONS

"Fitness Made Fun", WiiFit , Instruction Booklet, copyright 2008 Nintendo, 28 pages.
(Continued)

*Primary Examiner* — Sundhara Ganesan
(74) *Attorney, Agent, or Firm* — Pillsbury Winthrop Shaw Pittman LLP (57) ABSTRACT

A personal wellness system may facilitate merchandizing and/or socializing via personal wellness devices. The personal wellness devices may be portable, handheld devices configured to facilitate personal exercise as well as socializing and/or merchandizing using the devices. The personal wellness devices may be configured to facilitate electronic social networking interactions and/or gameplay with other users. This may enhance a user's personal wellness experience with a personal wellness device. The personal wellness devices may provide a portal to a virtual marketplace, where online services, virtual goods, third-party software, games, media, guru content, and/or other information may be obtained. Third-party content may be developed for the personal wellness devices, which may be obtained via the virtual marketplace. The personal wellness devices may be configured to present multimedia, present map information, and/or browse the Internet.

18 Claims, 3 Drawing Sheets

(51) Int. Cl.
   *A61N 1/04*   (2006.01)
   *A61B 5/024*   (2006.01)
   *A61B 5/11*   (2006.01)
   *A61B 5/145*   (2006.01)
   *A61B 5/22*   (2006.01)

(52) U.S. Cl.
   CPC ............... *A61B 5/024* (2013.01); *A61B 5/11* (2013.01); *A61B 5/14532* (2013.01); *A61B 5/222* (2013.01)

(58) Field of Classification Search
   USPC .................................................... 482/1, 8, 9
   See application file for complete search history.

(56) References Cited

U.S. PATENT DOCUMENTS

| | | | |
|---|---|---|---|
| 4,824,103 A | 4/1989 | Smidt | 272/125 |
| 4,988,981 A | 1/1991 | Zimmerman | |
| 5,144,284 A | 9/1992 | Hammett | |
| 5,242,348 A | 9/1993 | Bates | 482/105 |
| 5,471,405 A | 11/1995 | Marsh | 364/556 |
| 5,702,323 A | 12/1997 | Poulton | |
| 5,720,711 A | 2/1998 | Bond et al. | 601/23 |
| 5,790,102 A | 8/1998 | Nassimi | 345/163 |
| 5,792,080 A | 8/1998 | Ookawa et al. | 601/115 |
| 5,890,995 A | 4/1999 | Bobick et al. | 482/4 |
| 5,904,639 A | 5/1999 | Smyser et al. | 482/91 |
| 5,923,318 A | 7/1999 | Zhai | |
| 5,982,342 A | 11/1999 | Iwata | |
| 5,997,489 A | 12/1999 | Iwamoto et al. | 601/73 |
| 6,013,007 A | 1/2000 | Root et al. | 482/8 |
| 6,063,045 A | 5/2000 | Wax | |
| 6,126,572 A | 10/2000 | Smith | 482/4 |
| 6,183,425 B1 | 2/2001 | Whalen et al. | 600/592 |
| 6,191,773 B1 | 2/2001 | Maruno | |
| 6,222,465 B1 | 4/2001 | Kumar | |
| 6,227,968 B1 | 5/2001 | Suzuki et al. | 463/7 |
| 6,324,557 B1 | 11/2001 | Chan | 708/142 |
| 6,359,611 B2 | 3/2002 | Chan | 345/156 |
| 6,360,597 B1 | 3/2002 | Hubbard, Jr. | 73/172 |
| 6,405,278 B1 | 6/2002 | Liepe | 711/103 |
| 6,435,937 B1 | 8/2002 | Naegele | 446/298 |
| 6,513,532 B2 | 2/2003 | Mault et al. | 128/921 |
| 6,585,668 B2 | 7/2003 | Nissim | |
| 6,595,901 B2 | 7/2003 | Reinbold et al. | 482/91 |
| 6,597,347 B1 | 7/2003 | Yasutake | |
| 6,605,038 B1 | 8/2003 | Teller et al. | 600/300 |
| 6,616,579 B1 | 9/2003 | Reinbold et al. | 482/91 |
| 6,662,651 B1 | 12/2003 | Roth | 73/379.02 |
| 6,675,130 B2 | 1/2004 | Kanevsky et al. | 702/188 |
| 6,776,345 B1 | 8/2004 | Liang | 235/486 |
| 6,807,869 B2 | 10/2004 | Farringdon et al. | 73/862.046 |
| 6,837,827 B1 | 1/2005 | Lee et al. | 482/8 |
| 6,914,695 B2 | 7/2005 | Walters et al. | 358/1.15 |
| 6,956,833 B1 | 10/2005 | Yukie et al. | 370/328 |
| 6,975,644 B2 | 12/2005 | Tordera et al. | 370/463 |
| 7,026,940 B2 | 4/2006 | Cherubini | |
| 7,121,982 B2 | 10/2006 | Feldman | |
| 7,161,490 B2 | 1/2007 | Huiban | |
| 7,169,120 B2 | 1/2007 | Murdock et al. | 601/129 |
| 7,192,387 B2 | 3/2007 | Mendel | 482/8 |
| 7,229,385 B2 | 6/2007 | Freeman et al. | 482/4 |
| 7,292,867 B2 | 11/2007 | Werner et al. | 455/456.3 |
| 7,303,534 B2 | 12/2007 | Kahn | 600/587 |
| 7,398,151 B1 | 7/2008 | Burrell et al. | 701/200 |
| 7,429,251 B2 | 9/2008 | Tanizawa et al. | 601/94 |
| 7,468,968 B2 | 12/2008 | Svensson et al. | 370/338 |
| 7,480,512 B2 | 1/2009 | Graham et al. | 455/456.3 |
| 7,499,746 B2 | 3/2009 | Buhlmann et al. | 607/2 |
| 7,517,327 B1 | 4/2009 | Knight | 601/46 |
| 7,526,314 B2 | 4/2009 | Kennedy | 455/556.1 |
| 7,526,954 B2 | 5/2009 | Haselhurst et al. | 73/172 |
| RE40,891 E | 9/2009 | Yasutake | |
| 7,643,895 B2 | 1/2010 | Gupta et al. | 700/94 |
| 7,666,118 B1 | 2/2010 | Anthony | |
| 7,699,755 B2 | 4/2010 | Feldman | |
| 7,699,757 B2 | 4/2010 | Clem et al. | 482/49 |
| 7,702,821 B2 | 4/2010 | Feinberg et al. | 710/13 |
| 7,717,825 B2 | 5/2010 | Van Der Hoeven | |
| 7,758,469 B2 | 7/2010 | Dyer et al. | 482/4 |
| 7,789,800 B1 | 9/2010 | Watterson et al. | 482/8 |
| 7,840,346 B2 | 11/2010 | Huhtala et al. | 701/209 |
| 7,909,741 B2 | 3/2011 | Kim | |
| 7,975,543 B2 | 7/2011 | Clem et al. | 73/379.02 |
| 8,009,056 B2 | 8/2011 | Greene | |
| 8,025,606 B2 | 9/2011 | Hamilton | |
| 8,027,822 B2 | 9/2011 | Turgiss et al. | 703/11 |
| 8,172,723 B1 | 5/2012 | Yanev et al. | 482/8 |
| 8,200,323 B2 * | 6/2012 | DiBenedetto et al. | 600/519 |
| 8,203,454 B2 | 6/2012 | Knight | |
| 8,287,434 B2 | 10/2012 | Zavadsky | |
| 8,343,013 B1 | 1/2013 | Yanev et al. | 482/8 |
| 8,491,446 B2 | 7/2013 | Hinds | |
| 8,618,400 B2 | 12/2013 | Murphy | |
| 8,935,438 B1 | 1/2015 | Ivanchenko | |
| 2001/0049470 A1 | 12/2001 | Mault et al. | 600/300 |
| 2002/0146670 A1 | 10/2002 | Selles et al. | 434/247 |
| 2003/0020629 A1 | 1/2003 | Swartz et al. | 340/825.25 |
| 2003/0040688 A1 | 2/2003 | Bauer | 601/23 |
| 2003/0093012 A1 | 5/2003 | Smyser | |
| 2003/0137495 A1 | 7/2003 | Canova | |
| 2004/0021681 A1 | 2/2004 | Liao | 345/702 |
| 2004/0058305 A1 | 3/2004 | Lurie et al. | 434/265 |
| 2004/0110602 A1 | 6/2004 | Feldman | |
| 2004/0176226 A1 | 9/2004 | Carlson | |
| 2004/0260215 A1 | 12/2004 | Kim | 601/99 |
| 2005/0040999 A1 | 2/2005 | Numano | 345/1.1 |
| 2005/0130742 A1 * | 6/2005 | Feldman et al. | 463/39 |
| 2005/0177054 A1 | 8/2005 | Yi | |
| 2005/0209049 A1 | 9/2005 | Shields | 482/8 |
| 2005/0219355 A1 | 10/2005 | Tahara et al. | 348/14.05 |
| 2005/0283204 A1 | 12/2005 | Buhlmann | |
| 2006/0035762 A1 | 2/2006 | Smyser et al. | 482/91 |
| 2006/0064042 A1 | 3/2006 | Smyser et al. | 600/595 |
| 2006/0100899 A1 | 5/2006 | Tajima | 705/2 |
| 2006/0122819 A1 | 6/2006 | Carmel | |
| 2006/0247095 A1 | 11/2006 | Rummerfield | 482/1 |
| 2007/0155589 A1 | 1/2007 | Shimizu | |
| 2007/0024736 A1 | 2/2007 | Matsuda | |
| 2007/0051842 A1 | 3/2007 | Pryor | 242/378.3 |
| 2007/0184953 A1 | 8/2007 | Luberski | |
| 2007/0219059 A1 | 9/2007 | Schwartz et al. | 482/8 |
| 2007/0219469 A1 | 9/2007 | Vardy | |
| 2007/0232455 A1 | 10/2007 | Hanoun | |
| 2007/0249975 A1 | 10/2007 | Pan et al. | 601/118 |
| 2007/0270727 A1 | 11/2007 | KhorassaniZadeh | |
| 2008/0090703 A1 | 4/2008 | Rosenberg | 492/8 |
| 2008/0091762 A1 | 4/2008 | Neuhauser et al. | 709/201 |
| 2008/0096726 A1 | 4/2008 | Riley et al. | 482/8 |
| 2008/0100718 A1 | 5/2008 | Louks et al. | 348/211.2 |
| 2008/0101272 A1 | 5/2008 | Hayes et al. | 370/313 |
| 2008/0132388 A1 | 6/2008 | Clem | |
| 2008/0146336 A1 | 6/2008 | Feldman et al. | 463/37 |
| 2008/0161051 A1 | 7/2008 | Schobbert et al. | 455/558 |
| 2008/0171311 A1 | 7/2008 | Centen | |
| 2008/0261696 A1 | 10/2008 | Yamazaki et al. | 463/39 |
| 2008/0262918 A1 | 10/2008 | Wiener | 705/14 |
| 2008/0281234 A1 | 11/2008 | Goris | |
| 2008/0287832 A1 | 11/2008 | Collins et al. | 600/587 |
| 2008/0300055 A1 | 12/2008 | Lutnick | |
| 2009/0017993 A1 | 1/2009 | Khanicheh et al. | 482/49 |
| 2009/0025475 A1 | 1/2009 | DeBeliso et al. | 73/379.02 |
| 2009/0035740 A1 | 2/2009 | Reed et al. | 434/265 |
| 2009/0048021 A1 | 2/2009 | Lian et al. | 463/37 |
| 2009/0048070 A1 | 2/2009 | Vincent et al. | 482/8 |
| 2009/0069160 A1 | 3/2009 | Summers | 482/91 |
| 2009/0076855 A1 | 3/2009 | McCord | 705/3 |
| 2009/0098980 A1 | 4/2009 | Waters | |
| 2009/0144080 A1 | 6/2009 | Gray et al. | 705/2 |
| 2009/0148821 A1 | 6/2009 | Carkner et al. | 434/265 |
| 2009/0228068 A1 | 9/2009 | Buhlmann et al. | 607/48 |
| 2009/0286654 A1 | 11/2009 | Rice | |
| 2010/0021876 A1 | 1/2010 | Clash | 434/265 |

(56) References Cited

U.S. PATENT DOCUMENTS

| | | | |
|---|---|---|---|
| 2010/0265179 A1 | 1/2010 | Ram | 345/163 |
| 2010/0056341 A1 | 3/2010 | Ellis et al. | 482/9 |
| 2010/0069148 A1 | 3/2010 | Cargill | 463/25 |
| 2010/0087763 A1 | 4/2010 | Hane-Karr | 601/137 |
| 2010/0127983 A1 | 5/2010 | Irani | |
| 2010/0137105 A1 | 6/2010 | McLaughlin | 482/8 |
| 2010/0178981 A1 | 7/2010 | Holcomb et al. | 463/37 |
| 2010/0197462 A1 | 8/2010 | Piane | |
| 2010/0245239 A1 | 9/2010 | Sternberg | |
| 2010/0248822 A1 | 9/2010 | Migos et al. | 463/29 |
| 2010/0255862 A1 | 10/2010 | Mitsunaga et al. | 455/466 |
| 2010/0255957 A1 | 10/2010 | Clem et al. | 482/49 |
| 2010/0259472 A1 | 10/2010 | Radivojevic | |
| 2010/0273610 A1 | 10/2010 | Johnson | 482/9 |
| 2010/0292050 A1 | 11/2010 | DiBenedetto et al. | 482/9 |
| 2010/0292600 A1 | 11/2010 | DiBenedetto et al. | 600/520 |
| 2011/0035303 A1 | 2/2011 | Jakstadt et al. | 705/34 |
| 2011/0046687 A1 | 2/2011 | Naschberger | 607/3 |
| 2011/0086747 A1 | 4/2011 | Broderick | |
| 2011/0124470 A1 | 5/2011 | Spurling et al. | 482/13 |
| 2011/0125866 A1 | 5/2011 | Williams | 709/217 |
| 2011/0143769 A1 | 6/2011 | Jones | |
| 2011/0165998 A1 | 7/2011 | Lau et al. | 482/8 |
| 2011/0187660 A1 | 8/2011 | Hirata et al. | 345/173 |
| 2011/0251021 A1 | 10/2011 | Zavadsky et al. | 482/5 |
| 2011/0260987 A1 | 10/2011 | Zhao et al. | 345/173 |
| 2011/0291943 A1 | 12/2011 | Thorn et al. | 345/173 |
| 2011/0302694 A1 | 12/2011 | Wang | |
| 2012/0047465 A1 | 2/2012 | Noda | |
| 2012/0051596 A1 | 3/2012 | Darnell | |
| 2012/0058861 A1 | 3/2012 | Satut | |
| 2012/0066591 A1 | 3/2012 | Hackwell | 715/702 |
| 2012/0071732 A1 | 3/2012 | Grey et al. | 600/301 |
| 2012/0075236 A1 | 3/2012 | Kim | |
| 2012/0077163 A1 | 3/2012 | SucarSuccar | |
| 2012/0078113 A1 | 3/2012 | Whitestone | |
| 2012/0088553 A1 | 4/2012 | Nunes | |
| 2012/0098744 A1 | 4/2012 | Stinson | |
| 2012/0108394 A1 | 5/2012 | Jones et al. | 482/8 |
| 2012/0112922 A1 | 5/2012 | Hillis et al. | 340/657 |
| 2012/0113019 A1 | 5/2012 | Anderson | 345/173 |
| 2012/0116550 A1 | 5/2012 | Hoffman et al. | 700/91 |
| 2012/0126941 A1 | 5/2012 | Coggill | 340/5.54 |
| 2012/0150074 A1 | 6/2012 | Yanev et al. | 600/587 |
| 2012/0162080 A1 | 6/2012 | Cao | 345/168 |
| 2012/0260220 A1 | 10/2012 | Griffin | |
| 2012/0265112 A1 | 10/2012 | Chen | 601/115 |
| 2012/0274508 A1 | 11/2012 | Brown | |
| 2012/0306782 A1 | 12/2012 | Seo et al. | 345/173 |
| 2013/0009907 A1 | 1/2013 | Rosenberg | |
| 2013/0059696 A1 | 3/2013 | Hijmans et al. | 482/8 |
| 2013/0072301 A1 | 3/2013 | Mallinson | |
| 2013/0076649 A1 | 3/2013 | Myers | |
| 2013/0093679 A1 | 4/2013 | Dickinson | |
| 2013/0106155 A1 | 5/2013 | Chang | |
| 2013/0127748 A1 | 5/2013 | Vertegaal | |
| 2013/0127980 A1 | 5/2013 | Haddick | |
| 2013/0201316 A1 | 8/2013 | Binder | |
| 2013/0212674 A1 | 8/2013 | Boger | |
| 2013/0337974 A1 | 12/2013 | Yanev et al. | 482/8 |
| 2013/0337976 A1 | 12/2013 | Yanev et al. | 482/8 |
| 2013/0344919 A1 | 12/2013 | Kim | |
| 2013/0345608 A1 | 12/2013 | Ehrenreich | |
| 2014/0062682 A1 | 3/2014 | Birnbaum | |
| 2014/0123003 A1 | 5/2014 | Song | |
| 2014/0184496 A1 | 7/2014 | Gribetz | |
| 2014/0317722 A1 | 10/2014 | Tartz | |
| 2014/0333543 A1 | 11/2014 | Yanev et al. | 345/173 |
| 2014/0335494 A1 | 11/2014 | Yanev et al. | 434/262 |
| 2015/0015476 A1 | 1/2015 | Yanev et al. | 345/156 |
| 2015/0173993 A1 | 6/2015 | Walsh | |

FOREIGN PATENT DOCUMENTS

| | | |
|---|---|---|
| JP | 2006345990 | 12/2006 |
| JP | 2009142333 | 7/2009 |
| JP | 20105214094 | 7/2010 |
| JP | 2013172841 | 9/2013 |
| TW | 509566 | 1/1988 |
| TW | 201000175 A | 1/2010 |
| TW | 201300098 | 1/2013 |
| TW | 201301215 | 1/2013 |
| WO | WO 2007/025382 | 3/2007 |
| WO | WO 2012/078718 | 6/2012 |
| WO | WO 2013/192071 | 12/2013 |
| WO | WO 2013/192079 | 12/2013 |
| WO | WO 2013/192084 | 12/2013 |
| WO | 2014018049 | 1/2014 |
| WO | WO 2014/182729 | 11/2014 |
| WO | WO 2014/182735 | 11/2014 |
| WO | 2015006411 | 1/2015 |
| WO | 2015006413 | 1/2015 |

OTHER PUBLICATIONS

Jovanov et al., "A Wireless Body Area Network of Intelligent Motion Sensors for Computer Assisted Physical Rehabilitation", Journal of NeuroEngineering and Rehabilitation, Mar. 1, 2005, vol. 2, No. 6, retrieved from URL: http://www.jneuroengrehab.com/content/2/1/6, retrieved on Apr. 2, 2012, 10 pages.

Halfbakery, "Computer Mouse with Pressure Sensitive Button", printed from http://www.halfbakery.com/idea/Computer_20Mouse_20with_20pressure . . . , Cord, May 10, 2005, printed Apr. 4, 2014, 3 pages.

International Search Report and Written Opinion dated Apr. 20, 2012 for corresponding International Patent Application No. PCT/US2011/063678 (7 pages).

International Search Report and Written Opinion dated Mar. 13, 2015 for corresponding International Patent Application No. PCT/US2014/037012, 9 pages.

International Search Report and Written Opinion dated Mar. 4, 2015 for corresponding International Patent Application No. PCT/US2014/037018, 9 pages.

International Search Report and Written Opinion dated Nov. 22, 2013 for corresponding International Patent Application No. PCT/US2013/046082 (7 pages).

International Search Report and Written Opinion dated Nov. 7, 2014 for corresponding International Patent Application No. PCT/EPUS2014/045899 (7 pages).

International Search Report and Written Opinion dated Oct. 1, 2013 for corresponding International Patent Application No. PCT/US2013/046096 (10 pages).

International Search Report and Written Opinion dated Oct. 2, 2013 for corresponding International Patent Application No. PCT/US2013/046118 (10 pages).

\* cited by examiner

MERCHANDIZING, SOCIALIZING, AND/OR GAMING VIA A PERSONAL WELLNESS DEVICE AND/OR A PERSONAL WELLNESS PLATFORM

FIELD OF THE INVENTION

The invention relates to facilitating merchandizing, socializing, and/or gaming via a personal wellness device and/or personal wellness platform.

BACKGROUND OF THE INVENTION

Apparatus used during personal exercise are typically considered either stationary or portable. Stationary apparatus may be configured to quantify various aspects of an exercise routine, such as number of repetitions, calories burnt, etc. Portable apparatus generally include much less functionality relative to larger, stationary apparatus. Neither stationary nor portable exercise apparatus typically include capabilities associated with merchandizing and/or socializing.

SUMMARY

One aspect of the invention relates to a personal wellness system configured to facilitate merchandizing and/or socializing via personal wellness devices, in accordance with one or more implementations. The personal wellness system may include one or more personal wellness devices. Individual ones of the personal wellness devices may be portable, handheld devices configured to facilitate personal exercise as well as socializing and/or merchandizing using the devices. According to some implementations, information may be transferred between at least one personal wellness device and other components of the personal wellness system. In exemplary implementations, the personal wellness devices may be configured to facilitate electronic social networking interactions and/or gameplay with other users. This may enhance a user's personal wellness experience with the personal wellness device. The personal wellness device may provide a portal to a virtual marketplace, where online services, virtual goods, third-party software, games, media, guru content, and/or other information may be obtained. In some implementations, third-party content may be developed for the personal wellness devices, which may be obtained via the virtual marketplace. The personal wellness device may be configured to present multimedia, present map information, and/or browse the Internet, in accordance with some implementations. The personal wellness devices may be configured to facilitate personal wellness management.

In addition to the personal wellness devices, the personal wellness system may include one or more of a user accessory, external resources, a personal computing platform, a personal wellness platform server, and/or other components, which may complement and/or include one or more functionalities attributed herein to the personal wellness devices. Components of the personal wellness system, such as the personal wellness devices, the personal computing platform, the personal wellness platform server, the user accessory, and/or the external resources, may be operatively linked via one or more electronic communication links.

A given personal wellness device may include one or more of a force sensor, a geo-location sensor, a motion sensor, a heart rate sensor, a blood glucose sensor, a biometric sensor, a pedometer, an electrical muscle stimulation (EMS) interface, a camera device, an actuator, a user interface, the communications apparatus, a power supply, the electronic storage, a processor, and/or other components. One or more components of the personal wellness device may be housed by one or more housing bodies. In implementations having two housing bodies, a first housing body and a second housing body may be movably coupled together by way of a coupling mechanism such that the two housing bodies are reconfigurable between an open configuration and a closed configuration. The two housing bodies may be configured to receive compressive force during personal exercise while in the closed configuration.

The force sensor may be configured to generate a force output signal that conveys information related to compressive force exerted on the personal wellness device. The geo-location sensor may be configured to generate a location output signal conveying information related to a geo-location of the personal wellness device. The motion sensor may be configured to generate a motion output signal that conveys information related to a motion and/or orientation of the personal wellness device. The heart rate sensor may be configured to generate a heart rate output signal that conveys information related to a heart rate of a user associated with the personal wellness device. The blood glucose sensor may be configured to generate a glucose output signal that conveys information related to a concentration of glucose in the blood of a user associated with the personal wellness device. The biometric sensor may be configured to generate a biometric output signal conveying information related to a biometric feature of a user. The pedometer may be configured to generate a step output signal that conveys information related to steps taken by a user carrying the personal wellness device. The electrical muscle stimulation interface may be configured to removably couple the personal wellness device with an electrode. The electrode may be configured to provide electrical muscle stimulation to a user. The camera device may be configured to capture visual data. The actuator may be configured to provide tactile feedback to a user. The communications apparatus may be configured to receive information and/or transmit information from the personal wellness device. The power supply may be configured to supply electrical power to one or more components of the personal wellness device. The electronic storage may be configured to electronically store information. The processor of the personal wellness device may be configured to execute computer program modules.

The user interface may be configured to receive information from a user and provide information to the user. As such, the user interface may include hardware and/or software to facilitate receiving information from the user and/or providing information to the user. Examples of input devices may include one or more of a touch screen, a touch pad, a keypad, a switch, an analog stick, a button, a dial, a microphone, biometric sensor, and/or other hardware configured to receive information from a user. Examples of output devices may include one or more of a display, touch screen, speakers, and/or other hardware configured to provide information to a user. According to some implementations, the user interface may be accessible by a user with the personal wellness device in an open configuration. With the personal wellness device in a closed configuration, all, some, or none of the user interface may be accessible by a user, in various implementations.

The user accessory may be configured to be physically and/or communicatively coupled with the personal wellness device. The user accessory may be configured extend exercise capabilities of the personal wellness device, provide therapy to a user of the personal wellness device, facilitate monitoring of one or more vital signs of a user of the personal wellness device, and/or extend other functionalities of the personal wellness device.

The personal computing platform may include one or more of electronic storage, at least one processor, and/or other components. The electronic storage may be configured to electronically store information. The processor may be configured to execute computer program modules. The personal computing platform may be configured to communicatively couple with the personal wellness device and/or other components of the personal wellness system. According to some implementations, the computing platform may include one or more of a personal computer, a laptop computer, a tablet computer, a Smart phone, a personal digital assistant (PDA), a gaming console, and/or other personal computing platforms.

The personal wellness platform server may include one or more of electronic storage, at least one processor, and/or other components. The electronic storage may be configured to electronically store information. The processor may be configured to execute computer program modules. The personal wellness platform server may be configured to communicatively couple with the personal wellness device and/or other components of the personal wellness system.

The processor(s) of the personal wellness device, the personal computing platform, and/or the personal wellness platform server may be configured to provide information processing capabilities in the personal wellness system. One or more of these processors may be configured to execute one or more of a device-platform communication module, a social networking module, a marketplace module, a gaming module, a multimedia module, a web browsing module, a mapping module, a content development module, and/or other computer program modules.

The device-platform communication module may be configured to facilitate transfer of information between at least one personal wellness device and other components of the personal wellness system such as, but not limited to, the personal computing platform and/or the personal wellness platform server. According to various implementations, information transferred between a personal wellness device and other components of the personal wellness system may include one or more exercise parameters based on tracked exercises, assistance with one or more exercises performed using the personal wellness device, an exercise regimen, alerts associated with scheduled exercises, a diet program, a force output signal and/or information derived therefrom, a location output signal and/or information derived therefrom, a motion output signal and/or information derived therefrom, and/or other information associated with the personal wellness system.

The social networking module may be configured to facilitate electronic social networking interactions between a user associated with a given personal wellness device and other users not associated with that personal wellness device. That is, the social networking interactions may occur between users of different personal wellness devices and/or between a user of a given personal wellness device and a user accessing a social network by a platform such as the personal computing platform. Social networking interactions may enable users of the personal wellness devices to form communities associated with personal wellness. In some implementations, the social networking module may be configured to interface with one or more third-party electronic social networking services to facilitate the electronic social networking interactions.

The marketplace module may be configured to provide a portal to a virtual market place. According to some implementations, the portal may include a website, application, and/or other point of access to the virtual market place. The portal may be provided for presentation via the user interface of a personal wellness device. The virtual marketplace may enable one or more of online services, virtual goods, third-party software, games, media, guru content, and/or other information to be obtained via the personal wellness device. Examples of online services may include one or more of an email service, news service, entertainment service, internet search service, banking service, and/or other online services. Virtual goods may include non-physical objects for use in online communities, online games, and/or other purposes online. Third-party software may be configured to be executed by the personal wellness device and/or other components of the personal wellness system. Games may include software executable by the personal wellness device that is configured to provide gameplay via the personal wellness device. Media may include graphics, images, audio, video, and/or other types of media. Guru content may include text, videos, and/or other media that includes information from fitness counselors, athletic trainers, sports doctors, and/or other sources of expert information associated with personal wellness.

The gaming module may be configured to facilitate one or more games to be played using the personal wellness device. A game played using the personal wellness device may include a single-player game and/or a multi-player game. A single-player game may be played by an individual player using the personal wellness device. Examples of single-player games may include one or more of games involving performing exercises using the personal wellness device, games involving dexterity and/or coordination using the personal wellness device, board games played against an artificial opponent, solitaire card games, card games played against an artificial opponent, dice games played against an artificial opponent, guessing games, and/or other games played by a single player.

A multi-player game may be played by two or more users of different personal wellness devices. A multi-player game may be played by a user of a given personal wellness device and a user participating in the multi-player game via a platform such as the personal computing platform. Participants of a multi-player game may be remotely located from each other. Examples of multi-player games may include one or more of games involving performing exercises using the personal wellness device, games involving dexterity and/or coordination using the personal wellness device, board games played against a live opponent, card games played against a live opponent, dice games played against a live opponent, and/or other games played by two or more players. Some multi-player games may include a combination of artificial and live opponents. According to some implementations, the gaming module may facilitate simulated physical games to be played using two or more the personal wellness devices. By way of a non-limiting example of such a simulated physical game, two users of separate personal wellness devices may engage in a "virtual arm wrestling" match in which each user applies a force to their respective personal wellness device and the user that applies a greater force over the duration of the match wins.

The multimedia module may be configured to facilitate multimedia content presentation via the user interface of a personal wellness device. Multimedia content may include movies, videos, audio, and/or other multimedia content. By way of non-limiting example, multimedia content may include instructional exercise videos. Multimedia content may be stored by electronic storage of the personal wellness device. In some implementations, multimedia content may be streamed from a component of the personal wellness system to the personal wellness device via the device-platform communication module for playback by the personal wellness device. For example, multimedia content may be stored by electronic storage of the personal computing platform, by electronic storage of the personal wellness platform server, and/or by other components of the personal wellness system such that the multimedia content can be streamed to the personal wellness device. Multimedia content may be uploaded by a user to the personal wellness device and/or other components of the personal wellness system. Multimedia content may be obtained via a virtual marketplace accessible with the marketplace module.

The web browsing module may be configured to facilitate web browsing via the user interface of a personal wellness device. Web browsing may include retrieving, presenting, and/or traversing information resources on the World Wide Web. An information resource may be identified by a Uniform Resource Identifier (URI) and may include a web page, image, video, and/or other online content. Hyperlinks present in information resources may enable users to navigate to other information resources. In some implementations, the web browsing module may provide a web browser for presentation and user interaction via the user interface. A web browser may include an application software or program designed to enable retrieval, presentation, and/or traversal of documents and/or other information resources on the Internet. Some non-limiting examples of web browsers may include Firefox™, Google Chrome™, Internet Explorer™, Opera™, Safari™, and/or other web browsers.

The mapping module may be configured to provide map information for presentation via the user interface of the personal wellness device. Map information may include map images, other graphic representations of a geographic local or region, and/or other information associated with maps and/or geographic locations. In some implementations, map information may show a current geo-location of the personal wellness device. A current geo-location of the personal wellness device may be determined based on a location output signal generated by the geo-location sensor. The mapping module may indicate a geo-location of one or more other users of personal wellness devices. The mapping module may provide driving and/or walking directions. For example, the mapping module may indicate a route to be taken during various exercises, such as running, walking, biking, and/or other locomotive exercises. The mapping module may record a route taken during various exercises, such as running, walking, biking, and/or other locomotive exercises. Map information may be stored by electronic storage of the personal wellness device. In some implementations, map information may be stored by electronic storage of the personal computing platform, by electronic storage of the personal wellness platform server, and/or by other components of the personal wellness system such that the map information can be accessed by the personal wellness device.

The content development module may be configured to facilitate developing third-party content. The third-party content may be configured for presentation via the user interface of the personal wellness device. Third-party content may include non-executable content and executable content. Non-executable content may include text, movies, videos, audio, and/or other non-executable content. Executable content may include computer software programs configured to be executed by processors such as the processor(s) of the personal wellness device. Third-party content may be obtained by a virtual marketplace accessible via the marketplace module and/or other sources of third-party content in the personal wellness system. The content development module may provide a software development kit (SDK) associated with the personal wellness device. The SDK may enable developers to create third-party content.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
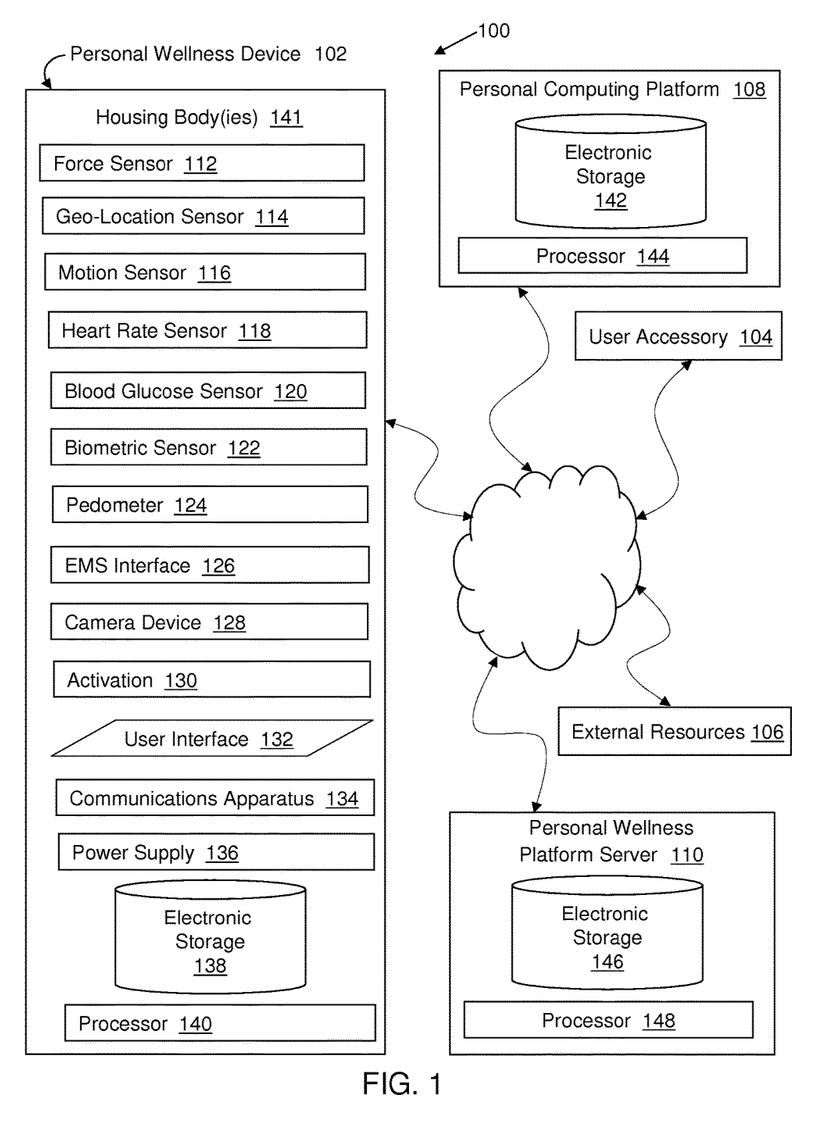
FIG. 1 illustrates a personal wellness system configured to facilitate merchandizing and/or socializing via personal wellness devices, in accordance with one or more implementations.

FIG. 1 illustrates a personal wellness system 100 configured to facilitate merchandizing and/or socializing via personal wellness devices, in accordance with one or more implementations. The personal wellness system 100 may include one or more personal wellness devices 102. Individual ones of the personal wellness devices 102 may be portable, handheld devices configured to facilitate personal exercise as well as socializing and/or merchandizing using the devices. According to some implementations, information may be transferred between at least one personal wellness device 102 and other components of personal wellness system 100. In exemplary implementations, personal wellness device 102 may be configured to facilitate electronic social networking interactions and/or gameplay with other users. This may enhance a user's personal wellness experience with personal wellness device 102. The personal wellness device 102 may provide a portal to a virtual marketplace, where online services, virtual goods, third-party software, games, media, guru content, and/or other information may be obtained. In some implementations, third-party content may be developed for personal wellness device 102, which may be obtained via the virtual marketplace. The personal wellness device 102 may be configured to present multimedia, present map information, and/or browse the Internet, in accordance with some implementations. The personal wellness device 102 may be configured to facilitate personal wellness management, as described in U.S. patent application Ser. No. 13/527,401, filed on Jun. 19, 2012, and entitled "Personal Wellness Management Platform," which is incorporated herein by reference.

In addition to personal wellness device 102, personal wellness system 100 may include one or more of a user accessory 104, external resources 106, a personal computing platform 108, a personal wellness platform server 110, and/or other components, which may complement and/or include one or more functionalities attributed herein to personal wellness device 102. Components of personal wellness system 100, such as personal wellness device 102, personal computing platform 108, personal wellness platform server 110, user accessory 104, and/or external resources 106, may be operatively linked via one or more electronic communication links. For example, such electronic communication links may be established, at least in part, via a wired or wireless network, which may include the Internet, WiFi, LAN, Bluetooth, and/or other networks. It will be appreciated that this is not intended to be limiting, and that the scope of this disclosure includes implementations in which personal wellness device 102, personal computing platform 108, personal wellness platform server 110, user accessory 104, and/or external resources 106 are operatively linked via some other communication media.

As depicted in FIG. 1, personal wellness device 102 may include one or more of a force sensor 112, a geo-location sensor 114, a motion sensor 116, a heart rate sensor 118, a blood glucose sensor 120, a biometric sensor 122, a pedometer 124, an electrical muscle stimulation (EMS) interface 126, a camera device 128, an actuator 130, a user interface 132, communications apparatus 134, a power supply 136, electronic storage 138, a processor 140, and/or other components, all housed by one or more housing body(ies) 141. According to some implementations, housing body(ies) 141 may comprise two housing bodies including a first housing body and a second housing body. The first housing body and the second housing body may be movably coupled together by way of a coupling mechanism such that the two housing bodies are reconfigurable between an open configuration and a closed configuration. The two housing bodies may be configured to receive compressive force during personal exercise while in the closed configuration. The user interface 132 may be accessible with the two housing bodies in the open configuration. Exemplary implementations of a personal wellness device having two housing bodies are described in U.S. patent application Ser. No. 13/527,465, filed on Jun. 19, 2012, and entitled "Personal Wellness Device," which is incorporated herein by reference.

The force sensor 112 may be configured to generate a force output signal that conveys information related to compressive force exerted on personal wellness device 102. Such information may include or be used to determine magnitude of force, duration of force, a force magnitude profile as a function of time, a quantity of compressive forces, and/or other information related to compressive force exerted on personal wellness device 102. The force output signal generated by force sensor 112 may be received and/or utilized by one or more modules executable by processor 140, as described further herein. By way of non-limiting example, force sensor 112 may include a FlexiForce A201 force sensor from Tekscan. However, other apparatus configured for force sensing are contemplated and within the scope of the invention.

The geo-location sensor 114 may be configured to generate a location output signal conveying information related to a geo-location of personal wellness device 102. The location output signal may be used to quantify one or more parameters of personal exercise. Such parameters may include speed, distance traveled, course of travel, and/or other parameters related to a geo-location of personal wellness device 102. By way of non-limiting example, geo-location sensor 114 may include a GPS device and/or other device configured to generate signals related to geo-location. However, other apparatus and techniques for location sensing and/or detecting are contemplated and within the scope of the invention.

The motion sensor 116 may be configured to generate a motion output signal that conveys information related to a motion and/or orientation of personal wellness device 102. The motion output signal may be used to quantify motions, changes in motion, orientation, changes in orientation, and/or information derived therefrom. By way of non-limiting example, motion sensor 116 may include an accelerometer configured to generate signals related to motion and/or orientation. However, other apparatus and techniques for motion and/or orientation sensing and/or detection are contemplated and within the scope of the invention.

The heart rate sensor 118 may be configured to generate a heart rate output signal that conveys information related to a heart rate of a user associated with personal wellness device 102. The heart rate sensor 118 may utilize electrocardiography (ECG or EKG). The heart rate output signal may be used to monitor heart rate in real time or record heart rate data for later observation and/or analysis. In some implementations, heart rate sensor 118 is integrated into personal wellness device 102 such that heart rate sensor 118 may measure a user's heart rate by way of physical contact between the user and personal wellness device 102. The heart rate sensor 118 may communicatively couple with a heart rate monitor that is separate and distinct from personal wellness device 102, according to some implementations. Examples of separate and distinct heart rate monitors may include a chest strap, a finger clip, a garment with an integrated heart rate monitor, and/or other devices configured to probe heart rate.

The blood glucose sensor 120 may be configured to generate a glucose output signal that conveys information related to a concentration of glucose in the blood of a user associated with personal wellness device 102. The glucose output signal may be used to determine a concentration of glucose and/or information derived therefrom. In some implementations, blood glucose sensor 120 may require a blood sample from a user in order to generate the glucose output signal. The blood glucose sensor 120 may be based on one or more non-invasive technologies including near IR detection, ultrasound, dielectric spectroscopy, and/or other non-invasive technologies for determining glucose concentration, in accordance with some implementations.

The biometric sensor 122 may be configured to generate a biometric output signal conveying information related to a biometric feature of a user. The biometric output signal may be used to identify and/or authenticate a user of personal wellness device 102. A biometric feature of a user may include physiological characteristics related to the shape of the body of the user. Examples of physiological characteristics may include particular geometries of a fingerprint, face, palm, hand, iris, retina, and/or other physiological characteristics. The biometric sensor 122 may include an image capture device, a biometric scanner, and/or other device configured to observe biometric features. In some implementations, biometric sensor 122 is included in user interface 132.

The pedometer 124 may be configured to generate a step output signal that conveys information related to steps taken by a user carrying personal wellness device 102. The step output signal may be used to determine a number of steps taken, a distance traveled, and/or other information related to or derived from steps taken by a user. In some implementations, pedometer 124 may include a separate and distinct device communicatively coupled with personal wellness device 102 and configured to transmit the step output signal to personal wellness device 102.

The electrical muscle stimulation interface 126 may be configured to removably couple personal wellness device 102 with an electrode. The electrode may be configured to provide electrical muscle stimulation to a user. In some implementations, electronic pulses (or other waveforms) may be provided by electrical muscle stimulation interface 126 to the electrode, which in turn may deliver the electrical pulses to a surface area of a user's body causing proximate muscles to exercise passively.

The camera device 128 may be configured to capture visual data. The visual data may include still images, video, and/or other visual data. In some implementations, camera device 128 may be utilized as biometric sensor 122. The imaging device 114 may include, by way of non-limiting example, a digital camera and/or other imaging devices.

The actuator 130 may be configured to provide tactile feedback to a user. Tactile feedback may be preferable in some use scenarios, for example, where other feedback mechanisms such as audio or visual may be undesired. Tactile feedback may include forces, vibrations, motions, and/or other tactile feedback provided to the user. The actuator 130 may include a mechanical device configured to cause one or more motions of personal wellness device 102. In some implementations, actuator 130 may include an electric motor with an unbalanced mass on its driveshaft such that rotation of the driveshaft generates vibrations. One or more parameters of the tactile feedback may be varied to convey different information to a user. The parameters may include one or more of direction, source location, duration, frequency, amplitude, and/or other parameters.

The user interface 132 may be configured to receive information from a user and provide information to the user. As such, user interface 132 may include hardware and/or software to facilitate receiving information from the user and/or providing information to the user. Examples of input devices may include one or more of a touch screen, a touch pad, a keypad, a switch, an analog stick, a button, a dial, a microphone, biometric sensor, and/or other hardware configured to receive information from a user. Examples of output devices may include one or more of a display, touch screen, speakers, and/or other hardware configured to provide information to a user.

In some implementations, user interface 132 may be configured to present user configurable settings to the user. The user interface 132 may be configured to receive selections from the user of values for the user configurable settings. One or more user configurable settings may impact the current activity of one or more components of personal wellness device 102. By way of non-limiting example, the user configurable settings may activate and/or deactivate one or more components of personal wellness device 102, and/or may configure one or more aspects of operation of personal wellness device 102. The user configurable settings may be related to personal exercise and/or wellness of a user of personal wellness device 102. The user configurable settings may be provided to processor 140 of personal wellness device 102. The user configurable settings may be provided to one or more processors of user accessory 104, personal computing platform 108, personal wellness platform server 110, and/or other components of personal wellness system 100.

According to some implementations, user interface 132 may include force sensor 112. By way of non-limiting example, a force output signal generated by force sensor 112 may be used to generate a random number. Such random numbers may be used in games of chance and/or other games provided by personal wellness system 100. As another example, a force output signal generated by force sensor 112 may be used to input numerical values and/or other information into user interface 132. To illustrate, a user may enter his body height by exerting a relevant amount of pressure on personal wellness device 102 rather than entering it with a graphical slider or number pad.

The communications apparatus 134 may be configured to receive information and/or transmit information from personal wellness device 102. As such, communications apparatus 134 may include one or both of a wireless communications interface or a wired communications interface. Examples of a communications interface may include a wired or wireless transmitter, a wired or wireless receiver, and/or a combined wired or wireless transmitter and receiver. The communications apparatus 134 may be configured to communicatively couple personal wellness device 102 with a computing platform (e.g., personal computing platform 108 and/or personal wellness platform server 110) configured to receive and process information related to compressive force exerted on the two housing bodies, a user accessory that is separate and distinct from personal wellness device 102, and/or other components of personal wellness system 100.

The power supply 136 may be configured to supply electrical power to one or more components of personal wellness device 102. By way of non-limiting example, power supply 136 may include one or more of a battery, a capacitor, apparatus for receiving electrical power from an external source (e.g., a wall socket), and/or other power supplies. In some implementations, power supply 136 may be rechargeable. In one implementation, where communications apparatus 134 includes a USB port or other wired communications port, communications apparatus 134 may receive electrical power from a component of personal wellness system 100 and/or another source to recharge power supply 136.

The electronic storage 138 may be configured to electronically store information. Exemplary implementations of electronic storage that is the same or similar to electronic storage 138 are described further herein.

The processor 140 may be configured to execute computer program modules. Exemplary implementations of processors that are the same or similar to processor 140 are described in connection with FIG. 2.

The user accessory 104 may be configured to be physically and/or communicatively coupled with personal wellness device 102. The user accessory 104 may be configured extend exercise capabilities of personal wellness device 102, provide therapy to a user of personal wellness device 102, facilitate monitoring of one or more vital signs of a user of personal wellness device 102, and/or extend other functionalities of personal wellness device 102.

In implementations where user accessory 104 is configured to extend exercise capabilities of personal wellness device 102, user accessory 104 may include a strap (not depicted in FIG. 1) or other apparatus configured for similar functionality attributed herein to the strap. Such a strap may be configured to physically couple to personal wellness device 102 and facilitate exertion of compressive force on personal wellness device 102 responsive to a tensive force exerted on the strap. The strap may be removably coupled to personal wellness device 102 by hooks, snaps, hook and loop fasteners, and/or other means for removable coupling.

In implementations where user accessory 104 is configured to provide therapy to a user of personal wellness device 102, user accessory 104 may include an electrode (not depicted in FIG. 1). In some implementations, electrical muscle stimulation interface 126 may be configured to removably couple personal wellness device 102 with the electrode. The electrode may be configured to provide electrical muscle stimulation to a user.

In implementations where user accessory 104 is configured to facilitate monitoring of one or more vital signs of a user of personal wellness device 102, user accessory 104 may include one or more accessories configured to facilitate monitoring of one or more of body temperature, heart rate, respiration rate, blood pressure, body sweat, and/or other vital signs. In some implementations, user accessory 104 may include a chest strap, a finger clip, a garment with an integrated heart rate monitor, and/or other devices configured to probe heart rate, which may communicatively couple with heart rate sensor 118. In some implementations, user accessory 104 may include a blood pressure sensor. The blood pressure sensor may be configured to generate a blood pressure output signal that conveys information related to a blood pressure of a user associated with personal wellness device 102.

In implementations where user accessory 104 is configured to extend other functionalities of personal wellness device 102, user accessory 104 may include one or more of a wired headset, a wireless headset, wired headphones, wireless headphones, a device that includes a display, a device configured to optically determine user and/or body part motion and/or position (e.g., MS Kinect™), and/or other accessories configured to extend one or more functionalities of personal wellness device 102.

The external resources 106 may include sources of information, hosts and/or providers of personal wellness systems, external entities participating with personal wellness system 100, and/or other resources. In some implementations, some or all of the functionality attributed herein to external resources 106 may be provided by resources included in personal wellness system 100.

The personal computing platform 108 may include one or more of electronic storage 142, at least one processor 144, and/or other components. The electronic storage 142 may be configured to electronically store information. Exemplary implementations of electronic storage that is the same or similar to electronic storage 142 are described further herein. The processor 144 may be configured to execute computer program modules. Exemplary implementations of processors that are the same or similar to processor 144 are described in connection with FIG. 2. The personal computing platform 108 may be configured to communicatively couple with personal wellness device 102 and/or other components of personal wellness system 100. The personal computing platform 108 may be configured to receive, transmit, process, and/or store information related to one or more of personal exercise, compressive force exerted on personal wellness device 102, and/or other information associated with personal wellness system 100. According to some implementations, the computing platform 104 may include one or more of a personal computer, a laptop computer, a tablet computer, a Smart phone, a personal digital assistant (PDA), a gaming console, and/or other personal computing platforms.

The personal wellness platform server 110 may include one or more of electronic storage 146, at least one processor 148, and/or other components. The electronic storage 146 may be configured to electronically store information. Exemplary implementations of electronic storage that is the same or similar to electronic storage 146 are described further herein. The processor 148 may be configured to execute computer program modules. Exemplary implementations of processors that are the same or similar to processor 146 are described in connection with FIG. 2. The personal wellness platform server 110 may be configured to communicatively couple with personal wellness device 102 and/or other components of personal wellness system 100. The personal wellness platform server 110 may be configured to receive, transmit, process, and/or store information related to one or more of personal exercise, compressive force exerted on personal wellness device 102, and/or other information associated with personal wellness system 100. In some implementations, personal wellness platform server 110 may be implemented by a cloud of computing platforms operating together as personal wellness platform server 110.

Electronic storage 138 of personal wellness device 102, electronic storage 142 of personal computing platform 108, and/or electronic storage 146 of personal wellness platform server 110 may comprise electronic storage media that electronically stores information. Such electronic storage media may include one or both of system storage that is provided integrally (i.e., substantially non-removable) with personal wellness device 102, personal computing platform 108, and/or personal wellness platform server 110. Electronic storage media may include removable storage that is removably connectable to personal wellness device 102, personal computing platform 108, and/or personal wellness platform server 110 via, for example, a port (e.g., a USB port, a firewire port, etc.) or a drive (e.g., a disk drive, etc.). Electronic storage 138, electronic storage 142, and/or electronic storage 146 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 138, electronic storage 142, and/or electronic storage 146 may include one or more virtual storage resources (e.g., cloud storage, a virtual private network, and/or other virtual storage resources). Electronic storage 138, electronic storage 142, and/or electronic storage 146 may store software algorithms; information determined by one or more processors (e.g., processor 140, processor 144, and/or processor 148); information received from personal wellness device 102, user accessory 104, external resources 106, personal computing platform 108, and/or personal wellness platform server 110; and/or other information that enables personal wellness system 100 to function as described herein.

Figure 2:
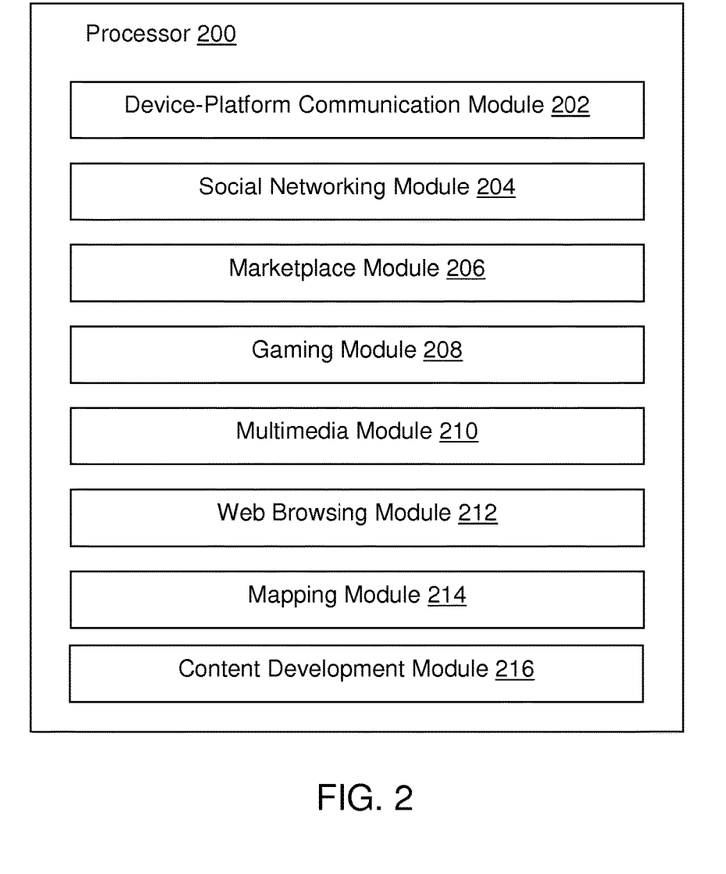
FIG. 2 illustrates an exemplary processor included in one or more components of the personal wellness system, in accordance with one or more implementations.

FIG. 2 illustrates an exemplary processor 200 included in one or more components of the personal wellness system, in accordance with one or more implementations. The processor 200 may be the same or similar to processor 140 of personal wellness device 102, processor 144 of personal computing platform 108, and/or processor 148 of personal wellness platform server 110. Processor 200 is configured to provide information processing capabilities in personal wellness system 100. As such, processor 200 may include one or more of a digital processor, an analog processor, a digital circuit designed to process information, an analog circuit designed to process information, a state machine, and/or other mechanisms for electronically processing information. Although processor 200 is shown in FIG. 2 as a single entity, this is for illustrative purposes only. In some implementations, processor 200 may include a plurality of processing units. These processing units may be physically located within the same device, or processor 200 may represent processing functionality of a plurality of devices operating in coordination.

As depicted in FIG. 2, processor 200 may be configured to execute one or more of a device-platform communication module 202, a social networking module 204, a marketplace module 206, a gaming module 208, a multimedia module 210, a web browsing module 212, a mapping module 214, a content development module 216, and/or other computer program modules. Processor 200 may be configured to execute modules 202, 204, 206, 208, 210, 212, 214, 216, and/or other modules by software; hardware; firmware; some combination of software, hardware, and/or firmware; and/or other mechanisms for configuring processing capabilities on processor 200.

It should be appreciated that although modules 202, 204, 206, 208, 210, 212, 214, and 216 are illustrated in FIG. 2 as being co-located within a single processing unit, in implementations in which processor 200 includes multiple processing units, one or more of modules 202, 204, 206, 208, 210, 212, 214, and/or 216 may be located remotely from the other modules. For example, one or more of modules 202, 204, 206, 208, 210, 212, 214, 216, and/or other modules may be executed by processor 140 of personal wellness device 102, processor 144 of personal computing platform 108, and/or processor 148 of personal wellness platform server 110. The description of the functionality provided by the different modules 202, 204, 206, 208, 210, 212, 214, and/or 216 described below is for illustrative purposes, and is not intended to be limiting, as any of modules 202, 204, 206, 208, 210, 212, 214, and/or 216 may provide more or less functionality than is described. For example, one or more of modules 202, 204, 206, 208, 210, 212, 214, and/or 216 may be eliminated, and some or all of its functionality may be provided by other ones of modules 202, 204, 206, 208, 210, 212, 214, and/or 216. As another example, processor 200 may be configured to execute one or more additional modules that may perform some or all of the functionality attributed below to one of modules 202, 204, 206, 208, 210, 212, 214, and/or 216.

The device-platform communication module 202 may be configured to facilitate transfer of information between at least one personal wellness device 102 and other components of personal wellness system 100 such as, but not limited to, personal computing platform 108 and/or personal wellness platform server 110. According to various implementations, information transferred between personal wellness device 102 and other components of personal wellness system 100 may include one or more exercise parameters based on tracked exercises, assistance with one or more exercises performed using personal wellness device 102, an exercise regimen, alerts associated with scheduled exercises, a diet program, a force output signal and/or information derived therefrom, a location output signal and/or information derived therefrom, a motion output signal and/or information derived therefrom, and/or other information associated with personal wellness system 100.

The social networking module 204 may be configured to facilitate electronic social networking interactions between a user associated with a given personal wellness device 102 and other users not associated with that personal wellness device 102. That is, the social networking interactions may occur between users of different personal wellness devices 102 and/or between a user of a given personal wellness device 102 and a user accessing a social network by a platform such as personal computing platform 108. Social networking interactions may enable users of personal wellness device 102 to form communities associated with personal wellness. In some implementations, social networking module 204 may be configured to interface with one or more third-party electronic social networking services to facilitate the electronic social networking interactions.

As used herein, a "social network" and/or "social networking service" may include one or more interactive, electronic social media, and/or other virtual environments. Interactive, electronic social media may include one or more of an electronic social network, a micro-blogging service, a blog service (or host), a messaging service, a message board, a forum, and/or other electronically distributed media that are scalable and enable interaction between the users. Some non-limiting specific examples of interactive, electronic social media may include the social network provided by Facebook™, the social network provided by MySpace™, the social network provided by Google+™, the social network provided by Qzone™, the social network provided by Foursquare®, the micro-blogging service provided by Twitter™, the virtual world provided by SecondLife®, the massively multi-player online game provided by World of Warcraft®, the file sharing service provided by Flickr®, Blogger, YouTube, PlayStation® Home, Xbox® Live, and/or other interactive, electronic social media.

The marketplace module 206 may be configured to provide a portal to a virtual market place. According to some implementations, the portal may include a website, application, and/or other point of access to the virtual market place. The portal may be provided for presentation via user interface 132 of personal wellness device 102. The virtual marketplace may enable one or more of online services, virtual goods, third-party software, games, media, guru content, and/or other information to be obtained via personal wellness device 102. Examples of online services may include one or more of an email service, news service, entertainment service, internet search service, banking service, and/or other online services. Virtual goods may include non-physical objects for use in online communities, online games, and/or other purposes online. Third-party software may be configured to be executed by personal wellness device 102 and/or other components of personal wellness system 100. Games may include software executable by personal wellness device 102 that is configured to provide gameplay via personal wellness device 102. Media may include graphics, images, audio, video, and/or other types of media. Guru content may include text, videos, and/or other media that includes information from fitness counselors, athletic trainers, sports doctors, and/or other sources of expert information associated with personal wellness.

The gaming module 208 may be configured to facilitate one or more games to be played using personal wellness device 102. A game played using personal wellness device 102 may include a single-player game and/or a multi-player game. A single-player game may be played by an individual player using personal wellness device 102. Examples of single-player games may include one or more of games involving performing exercises using personal wellness device 102, games involving dexterity and/or coordination using personal wellness device 102, board games played against an artificial opponent, solitaire card games, card games played against an artificial opponent, dice games played against an artificial opponent, guessing games, and/or other games played by a single player.

A multi-player game may be played by two or more users of different personal wellness devices 102. A multi-player game may be played by a user of a given personal wellness device 102 and a user participating in the multi-player game via a platform such as personal computing platform 108. Participants of a multi-player game may be remotely located from each other. Examples of multi-player games may include one or more of games involving performing exercises using personal wellness device 102, games involving dexterity and/or coordination using personal wellness device 102, board games played against a live opponent, card games played against a live opponent, dice games played against a live opponent, and/or other games played by two or more players. Some multi-player games may include a combination of artificial and live opponents. According to some implementations, gaming module 208 may facilitate simulated physical games to be played using two or more personal wellness devices 102. By way of a non-limiting example of such a simulated physical game, two users of separate personal wellness devices 102 may engage in a "virtual arm wrestling" match in which each user applies a force to their respective personal wellness device 102 and the user that applies a greater force over the duration of the match wins.

The multimedia module 210 may be configured to facilitate multimedia content presentation via user interface 132 of personal wellness device 102. Multimedia content may include movies, videos, audio, and/or other multimedia content. By way of non-limiting example, multimedia content may include instructional exercise videos. Multimedia content may be stored by electronic storage 138 of personal wellness device 102. In some implementations, multimedia content may be streamed from a component of personal wellness system 100 to personal wellness device 102 via device-platform communication module 202 for playback by personal wellness device 102. For example, multimedia content may be stored by electronic storage 144 of personal computing platform 108, by electronic storage 148 of personal wellness platform server 110, and/or by other components of personal wellness system 100 such that the multimedia content can be streamed to personal wellness device 102. Multimedia content may be uploaded by a user to personal wellness device 102 and/or other components of personal wellness system 100. Multimedia content may be obtained via a virtual marketplace accessible with marketplace module 206.

The web browsing module 212 may be configured to facilitate web browsing via user interface 132 of personal wellness device 102. Web browsing may include retrieving, presenting, and/or traversing information resources on the World Wide Web. An information resource may be identified by a Uniform Resource Identifier (URI) and may include a web page, image, video, and/or other online content. Hyperlinks present in information resources may enable users to navigate to other information resources. In some implementations, web browsing module 212 may provide a web browser for presentation and user interaction via user interface 132. A web browser may include an application software or program designed to enable retrieval, presentation, and/or traversal of documents and/or other information resources on the Internet. Some non-limiting examples of web browsers may include Firefox™, Google Chrome™, Internet Explorer™, Opera™, Safari™, and/or other web browsers.

The mapping module 214 may be configured to provide map information for presentation via user interface 132 of personal wellness device 102. Map information may include map images, other graphic representations of a geographic local or region, and/or other information associated with maps and/or geographic locations. In some implementations, map information may show a current geo-location of personal wellness device 102. A current geo-location of personal wellness device 102 may be determined based on a location output signal generated by geo-location sensor 114. The mapping module 214 may indicate a geo-location of one or more other users of personal wellness devices 102. The mapping module 214 may provide driving and/or walking directions. For example, mapping module 214 may indicate a route to be taken during various exercises, such as running, walking, biking, and/or other locomotive exercises. The mapping module 214 may record a route taken during various exercises, such as running, walking, biking, and/or other locomotive exercises. Map information may be stored by electronic storage 138 of personal wellness device 102. In some implementations, map information may be stored by electronic storage 144 of personal computing platform 108, by electronic storage 148 of personal wellness platform server 110, and/or by other components of personal wellness system 100 such that the map information can be accessed by personal wellness device 102.

The content development module 216 may be configured to facilitate developing third-party content. The third-party content may be configured for presentation via user interface 132 of personal wellness device 102. Third-party content may include non-executable content and executable content. Non-executable content may include text, movies, videos, audio, and/or other non-executable content. Executable content may include computer software programs configured to be executed by processors such as processor 140 of personal wellness device 102. Third-party content may be obtained by a virtual marketplace accessible via marketplace module 206 and/or other sources of third-party content in personal wellness system 100. The content development module 216 may provide a software development kit (SDK) associated with personal wellness device 102. The SDK may enable developers to create third-party content.

Figure 3:
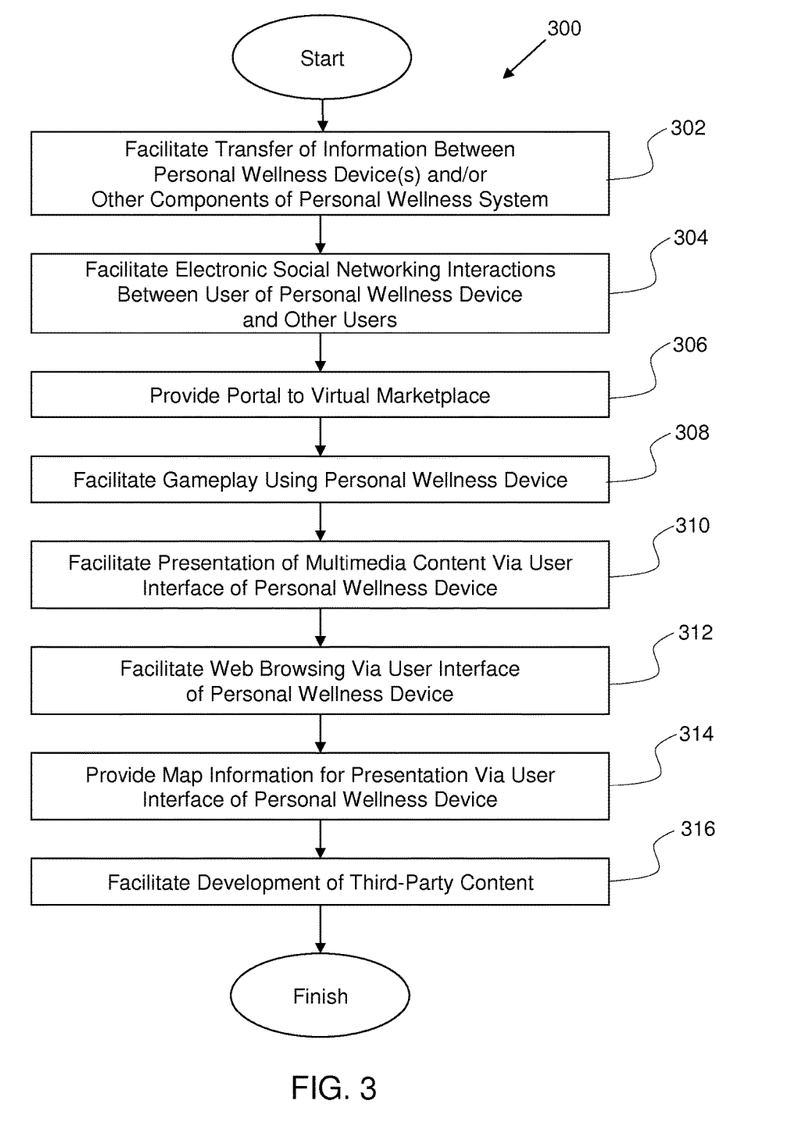
FIG. 3 illustrates a method for facilitating merchandizing and/or socializing via a personal wellness device, in accordance with one or more implementations.

FIG. 3 illustrates a method 300 for facilitating merchandizing and/or socializing via a personal wellness device, in accordance with one or more implementations. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, transfer of information may be facilitated between at least one personal wellness device 102 and other components of personal wellness system 100 such as, but not limited to, personal computing platform 108 and/or personal wellness platform server 110. Operation 302 may be performed by a device-platform communication module that is the same as or similar to device-platform communication module 202, in accordance with one or more implementations.

At an operation 304, electronic social networking interactions may be facilitated between a user associated with a given personal wellness device 102 and other users not associated with that personal wellness device 102. Operation 304 may be performed by a social networking module that is the same as or similar to social networking module 204, in accordance with one or more implementations.

At an operation 306, a portal to a virtual marketplace may be provided. Operation 306 may be performed by a marketplace module that is the same as or similar to marketplace module 206, in accordance with one or more implementations.

At an operation 308, gameplay using personal wellness device 102 of one or more games may be facilitated. Operation 308 may be performed by a gaming module that is the same as or similar to gaming module 208, in accordance with one or more implementations.

At an operation 310, presentation of multimedia content via user interface 132 of personal wellness device 102 may be facilitated. Operation 310 may be performed by a multimedia module that is the same as or similar to multimedia module 210, in accordance with one or more implementations.

At an operation 312, web browsing via user interface 132 of personal wellness device 102 may be facilitated. Operation 312 may be performed by a web browsing module that is the same as or similar to web browsing module 212, in accordance with one or more implementations.

At an operation 314, map information may be provided for presentation via user interface 132 of personal wellness device 102. Operation 314 may be performed by a mapping module that is the same as or similar to mapping module 214, in accordance with one or more implementations.

At an operation 316, development of third-party content may be facilitated. Operation 316 may be performed by a content development module that is the same as or similar to content development module 216, in accordance with one or more implementations.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A personal wellness device configured to provide one or more of socializing or merchandizing services to a user of the personal wellness device, the personal wellness device comprising:
    at least one housing body configured to receive compressive force during personal exercise;
    a force sensor configured to generate a force output signal that conveys first information related to compressive force exerted on the at least one housing body, the force sensor being housed by the at least one housing body;
    a user interface comprising one or more input devices and one or more output devices, the user interface being configured to receive user-provided information from the user via voice entry or manual entry, the user interface being further configured to provide information for one or both of visual or audio presentation to the user, the user interface being housed by the at least one housing body; and one or more physical processors housed by the at least one housing body, the one or more physical processors being configured by machine-readable instructions to:
        transmit via a network one or both of the first information or the user-provided information to a second personal wellness device associated with a second user via a personal computing platform and/or personal wellness platform server;
        receive secondary information via the network and the personal computing platform and/or personal wellness platform server from the second personal wellness device, the secondary information being related to compressive force exerted on a housing body of the second personal wellness device including a force magnitude profile as a function of time; and
        provide the secondary information for presentation to the user via the user interface.

2. The personal wellness device of claim 1, wherein the one or more physical processors are further configured by machine-readable instructions such that:
    one or both of the first information or the user-provided information transmitted via the network to the second personal wellness device is routed via the network through one or more third-party electronic social networking servers; and
    the secondary information received via the network from the second personal wellness device is routed via the network through the one or more third-party electronic social networking servers.

3. The personal wellness device of claim 1, wherein the one or more physical processors are further configured by machine-readable instructions to effectuate presentation of a website or application on the user interface, the website or application including a virtual marketplace, the virtual marketplace enabling one or more of online services, virtual goods, third-party software, games, media, or guru content to be accessed via the website or application.

4. The personal wellness device of claim 1, wherein the one or more physical processors are further configured by machine-readable instructions to:
    provide the force output signal as control inputs for controlling one or more games being executed by the one or more physical processors.

5. The personal wellness device of claim 1, wherein the one or more physical processors are further configured by machine-readable instructions to effectuate presentation of multimedia content via the user interface.

6. The personal wellness device of claim 1, wherein the one or more physical processors are further configured by machine-readable instructions to:
    effectuation transmission of information received from the user via the user interface to a web server;
    receive information from the web server; and
    provide the information received from the web server to the user via the user interface.

7. The personal wellness device of claim 1, wherein the one or more physical processors are further configured by machine-readable instructions to effectuate presentation of map images on the user interface.

8. The personal wellness device of claim 1, wherein the one or more physical processors are further configured by machine-readable instructions to:
receive information from a third-party user not associated with the personal wellness device, the information being associated with one or more of non-executable content or executable content, the one or more of the non-executable content or executable content being configured for presentation via the user interface.

9. A personal wellness platform configured to provide one or more of socializing or merchandizing services to users via individual personal wellness devices associated with individual users, the personal wellness platform comprising:
one or more physical processors configured by machine-readable instructions to:
facilitate transmission and reception of information via a network between the personal wellness platform and individual ones of the personal wellness devices including a first personal wellness device and a second personal wellness device; and
facilitate transmission and reception of information via the network and personal wellness platform server between individual ones of the personal wellness devices including between the first personal wellness device and the second personal wellness device;
wherein the first personal wellness device comprises:
at least one housing body configured to receive compressive force during personal exercise;
a force sensor configured to generate a force output signal that conveys first information related to compressive force exerted on the at least one housing body, the force sensor being housed by the at least one housing body;
a user interface comprising one or more input devices and one or more output devices, the user interface being configured to receive user-provided information from the user via voice entry or manual entry, the user interface being further configured to provide information for one or both of visual or audio presentation to the user the user interface being housed by the at least one housing body; and
one or more physical processors housed by the at least one housing body, the one or more physical processors being configured by machine-readable instructions to:
transmit via a network one or both of the first information or the user-provided information to the second personal wellness device associated with a second user;
receive secondary information via the network from the second personal wellness device, the secondary information being related to compressive force exerted on a housing body of the second personal wellness device including a force magnitude profile as a function of time; and
provide the secondary information for presentation to the user via the user interface.

10. The personal wellness platform of claim 9, wherein the one or more physical processors are further configured by machine-readable instructions such that one or more of the first information, the user-provided information, or the secondary information transmitted and received between individual ones of the personal wellness devices is routed via the network through one or more third-party electronic social networking servers.

11. The personal wellness platform of claim 9, wherein the one or more physical processors are further configured by machine-readable instructions to effectuate presentation of a website or application on user interfaces of individual ones of the personal wellness devices, the webpage or application including a virtual marketplace, the virtual marketplace enabling one or more of online services, virtual goods, third-party software, games, media, or guru content to be accessed via the website or application.

12. The personal wellness platform of claim 9, wherein the one or more physical processors are further configured by machine-readable instructions to:
provide individual force sensor outputs generated by individual force sensors of corresponding personal wellness devices as control inputs for controlling one or more games being executed by the corresponding personal wellness devices.

13. The personal wellness platform of claim 12, wherein individual ones of the one or more games are executed by groups of personal wellness devices, wherein individual personal wellness devices of a given group are remote from other ones of the personal wellness devices of the given group, and wherein a given game is played between individual users associated with individual personal wellness devises included in the given group.

14. The personal wellness platform of claim 9, wherein the one or more physical processors are further configured by machine-readable instructions to effectuate presentation of multimedia content via individual user interfaces of individual ones of the personal wellness devices.

15. The personal wellness platform of claim 9, wherein the one or more physical processors are further configured by machine-readable instructions to:
effectuate transmission of information received from individual users via individual user interfaces of individual personal wellness devices to one or more web servers;
receive information from the one or more web servers; and
provide the information received from the one or more web servers to individual ones of the personal wellness devices.

16. The personal wellness platform of claim 9, wherein the one or more physical processors are further configured by machine-readable instructions to effectuate presentation of map images on individual user interfaces of individual ones of the personal wellness devices.

17. The personal wellness platform of claim 16, wherein individual ones of the personal wellness devices include a geo-location sensor, a given geo-location sensor being configured to generate a location output signal related to a geo-location of a given personal wellness device in which the given geo-location sensor is included, and wherein a given map image presented on a given user interface of the given personal wellness device represents a current geo-location of the given personal wellness device determined from a corresponding location output signal.

18. The personal wellness platform of claim 9, wherein the one or more physical processors are further configured by machine-readable instructions to:
receive information from one or more third-party users not associated with the personal wellness devices, the information being associated with one or more of non-executable content or executable content, the one or more of the non-executable content or executable content being configured for presentation via individual user interfaces of individual ones of the personal wellness devices.

* * * * *

UNITED STATES PATENT AND TRADEMARK OFFICE
CERTIFICATE OF CORRECTION

PATENT NO. : 10,133,849 B2
APPLICATION NO. : 13/527437
DATED : November 20, 2018
INVENTOR(S) : Kostadin Dimitrov Yanev, Angel Georgiev Vassilev and Ivo Kostadinov Yanev It is certified that error appears in the above-identified patent and that said Letters Patent is hereby corrected as shown below:

On the Title Page

Under References Cited, U.S. PATENT DOCUMENTS, page 2, 2nd Column, Line 45:
Replace "2007/0155589 1/2007 Shimizu"
With --2007/0155589 7/2007 Feldman--

Under References Cited, U.S. PATENT DOCUMENTS, page 3, 1st Column, Line 1:
Replace "2010/0265179 A1 1/2010 Ram"
With --2010/0265179 A1 10/2010 Ram--

Signed and Sealed this
Twelfth Day of January, 2021

Andrei Iancu
*Director of the United States Patent and Trademark Office*